US012350057B2

United States Patent
Govari et al.

(10) Patent No.: US 12,350,057 B2
(45) Date of Patent: *Jul. 8, 2025

(54) ANALYZING MULTI-ELECTRODE CATHETER SIGNALS TO DETERMINE ELECTROPHYSIOLOGICAL (EP) WAVE PROPAGATION VECTOR

(71) Applicant: Biosense Webster (Israel) Ltd., Yokneam (IL)

(72) Inventors: Assaf Govari, Haifa (IL); Vadim Gliner, Haifa (IL); Yair Palti, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/362,158

(22) Filed: Jul. 31, 2023

(65) Prior Publication Data

US 2024/0023869 A1    Jan. 25, 2024

Related U.S. Application Data

(63) Continuation of application No. 16/918,972, filed on Jul. 1, 2020, now Pat. No. 11,730,413.

(51) Int. Cl.
*A61B 5/341* (2021.01)
*A61B 5/00* (2006.01)
(Continued)

(52) U.S. Cl.
CPC ............. *A61B 5/341* (2021.01); *A61B 5/287* (2021.01); *A61B 5/339* (2021.01); *A61B 5/343* (2021.01); *A61B 5/6858* (2013.01); *A61B 5/6859* (2013.01)

(58) Field of Classification Search
None
See application file for complete search history.

(56) References Cited

U.S. PATENT DOCUMENTS 6,226,542 B1   5/2001   Reisfeld
6,236,883 B1   5/2001   Ciaccio et al.
(Continued)

FOREIGN PATENT DOCUMENTS

CN   109069044 A   12/2018
CN   108348155 B   2/2019
(Continued)

OTHER PUBLICATIONS

Extended European Search Report dated Nov. 3, 2021, from corresponding EP Application No. 21182626.8.
(Continued)

*Primary Examiner* — Carl H Layno
*Assistant Examiner* — Manolis Pahakis

(57) ABSTRACT

A system comprising a processor and memory storing instructions configured to cause the system to: receive multiple electrophysiological (EP) signals acquired by multiple electrodes of a multi-electrode catheter that are in contact with tissue in a region of a cardiac chamber, and respective tissue locations at which the electrodes acquired the EP signals, calculate an average local activation time, determine: a first section of two sections having a smaller average LAT value, and a second section of the two sections having a higher average value, determine a first representative location in the first section, and a second representative location in the second section, calculate a propagation vector indicative of propagation of an EP wave that has generated the EP signals, determine if a re-entering EP wave is detected, and calculate an additional propagation vector for the re-entering EP wave.

20 Claims, 4 Drawing Sheets

(51) Int. Cl.
*A61B 5/287* (2021.01)
*A61B 5/339* (2021.01)
*A61B 5/343* (2021.01)

(56) References Cited

U.S. PATENT DOCUMENTS

| | | | |
|---|---|---|---|
| 6,301,496 | B1 | 10/2001 | Reisfeld |
| 6,892,091 | B1 | 5/2005 | Ben-Haim et al. |
| 7,536,218 | B2 | 5/2009 | Govari et al. |
| 7,756,576 | B2 | 7/2010 | Levin |
| 8,456,182 | B2 | 6/2013 | Bar-Tal et al. |
| 9,050,011 | B2 | 6/2015 | Rubinstein et al. |
| 10,842,572 | B1 | 11/2020 | Viswanathan |
| 11,439,339 | B1* | 9/2022 | Lux .................. A61B 5/346 |
| 2003/0023130 | A1 | 1/2003 | Ciaccio et al. |
| 2004/0243012 | A1 | 12/2004 | Ciaccio et al. |
| 2013/0079650 | A1* | 3/2013 | Turgeman .......... A61B 5/743 |
| | | | 600/509 |
| 2013/0245473 | A1* | 9/2013 | Ramanathan .......... A61B 5/318 |
| | | | 600/509 |
| 2013/0324871 | A1 | 12/2013 | Dubois et al. |
| 2014/0176531 | A1* | 6/2014 | Rubinstein .............. G06T 19/00 |
| | | | 345/419 |
| 2014/0336518 | A1* | 11/2014 | Shuros ................. A61B 5/6858 |
| | | | 600/509 |
| 2016/0045123 | A1* | 2/2016 | Bar-Tal .................. A61B 5/287 |
| | | | 600/515 |
| 2016/0089048 | A1 | 3/2016 | Brodnick et al. |
| 2016/0106376 | A1* | 4/2016 | Li .......................... A61B 5/349 |
| | | | 600/373 |
| 2017/0014086 | A1* | 1/2017 | Li ......................... A61B 5/6852 |
| 2017/0042449 | A1 | 2/2017 | Deno et al. |
| 2017/0049348 | A1 | 2/2017 | Deno et al. |
| 2017/0055864 | A1* | 3/2017 | Han ...................... A61B 5/316 |
| 2017/0202471 | A1 | 7/2017 | Urman et al. |
| 2017/0202515 | A1* | 7/2017 | Zrihem ................ A61B 5/6858 |
| 2017/0246461 | A1 | 8/2017 | Ghosh |
| 2017/0251942 | A1 | 9/2017 | Brodnick et al. |
| 2017/0281031 | A1* | 10/2017 | Houben .............. A61B 18/1492 |
| 2017/0311833 | A1 | 11/2017 | Afonso et al. |
| 2017/0332971 | A1 | 11/2017 | Macneil et al. |
| 2018/0153426 | A1 | 6/2018 | Thakur et al. |
| 2019/0069792 | A1* | 3/2019 | Shariat .................. A61B 5/316 |
| 2019/0076045 | A1 | 3/2019 | Katz et al. |
| 2019/0259490 | A1* | 8/2019 | Cohen .................... A61B 5/339 |
| 2019/0328258 | A1* | 10/2019 | Gaeta .................... A61B 5/282 |
| 2020/0060568 | A1* | 2/2020 | Katz .................... A61B 5/066 |
| 2020/0113465 | A1 | 4/2020 | Cohen et al. |
| 2020/0146579 | A1* | 5/2020 | Bar-Tal ................. A61B 5/349 |
| 2021/0127999 | A1* | 5/2021 | Govari .................. A61B 5/743 |
| 2021/0128006 | A1* | 5/2021 | Richer ................... A61B 5/364 |
| 2021/0133516 | A1* | 5/2021 | Govari .................. A61B 5/743 |
| 2021/0169421 | A1 | 6/2021 | Govari |
| 2021/0282659 | A1* | 9/2021 | Govari .................. A61B 5/367 |
| 2021/0361215 | A1* | 11/2021 | Deno ..................... A61B 5/341 |

FOREIGN PATENT DOCUMENTS

| | | |
|---|---|---|
| CN | 110179458 A | 8/2019 |
| CN | 110267586 A | 9/2019 |
| CN | 111035382 A | 4/2020 |
| CN | 111150390 A | 5/2020 |
| CN | 112639990 A | 4/2021 |
| EP | 3639740 A1 | 4/2020 |
| EP | 3649930 A1 | 5/2020 |
| JP | 2017514536 A | 6/2017 |
| JP | 2018526107 A | 9/2018 |
| JP | 2019177135 A | 10/2019 |
| JP | 2020062403 A | 4/2020 |
| JP | 2021512694 A | 5/2021 |
| WO | 2019156755 A1 | 8/2019 |

OTHER PUBLICATIONS

Extended European Search Report dated Nov. 9, 2022, from corresponding EP Application No. 22180070.9.
Search Report with English translation dated Feb. 12, 2025, from corresponding Japanese Application No. 2021-108540.
Notice of Reasons for Refusal with English translation dated Feb. 18, 2025, from corresponding Japanese Application No. 2021-108540.
Written Opinion with English translation dated Apr. 17, 2025, from corresponding Japanese Application No. JP2021-108540.
First Search dated May 21, 2025, from corresponding Chinese Application No. 202110747722.3.
First Office Action with English translation dated May 21, 2025, from corresponding Chinese Application No. 202110747722.3.

* cited by examiner

ANALYZING MULTI-ELECTRODE CATHETER SIGNALS TO DETERMINE ELECTROPHYSIOLOGICAL (EP) WAVE PROPAGATION VECTOR

The present application is a continuation application of U.S. patent application Ser. No. 16/918,972, filed Jul. 1, 2020 (now, U.S. Pat. No. 11,730,413), the entire contents of each of which is incorporated herein by reference in its entirety as if fully set forth herein.

FIELD OF THE INVENTION

The present invention relates generally to electrophysiological mapping, and particularly to cardiac electrophysiological mapping.

BACKGROUND OF THE INVENTION

Invasive cardiac techniques for mapping electrophysiological (EP) properties of cardiac tissue were previously proposed in the patent literature. For example, U.S. Patent Application Publication 2017/0311833 describes an efficient system for diagnosing arrhythmias and directing catheter therapies that may allow for measuring, classifying, analyzing, and mapping spatial EP patterns within a body. The efficient system may further guide arrhythmia therapy and update maps as treatment is delivered. The efficient system may use a medical device having a high density of sensors with a known spatial configuration for collecting EP data and positioning data. Further, the efficient system may also use an electronic control system for computing and providing the user with a variety of metrics, derivative metrics, high definition (HD) maps, HD composite maps, and general visual aids for association with a geometrical anatomical model shown on a display device.

As another example, U.S. Patent Application Publication 2017/0042449 describes a system for determining EP data, the system comprising an electronic control unit configured to acquire electrophysiology signals from a plurality of electrodes of one or more catheters, select at least one clique of electrodes from the plurality of electrodes to determine a plurality of local E field data points, determine the location and orientation of the plurality of electrodes, process the electrophysiology signals from the at least one clique from a full set of bi-pole sub-cliques to derive the local E field data points associated with the at least one clique of electrodes, derive at least one orientation independent signal from the at least one clique of electrodes from the information content corresponding to weighted parts of electrogram signals, and display or output catheter-orientation-independent EP information to a user or process.

U.S. Patent Application Publication 2018/0153426 describes method and system for mapping an anatomical structure, that include sensing activation signals of intrinsic physiological activity with a plurality of mapping electrodes disposed in or near the anatomical structure, each of the plurality of mapping electrodes having an electrode location. A vector field map which represents a direction of propagation of the activation signals at each electrode location is generated to identify a signature pattern and a location in the vector field map according to at least one vector field template. A target location of the identified signature pattern is identified according to a corresponding electrode location.

SUMMARY OF THE INVENTION

An embodiment of the present invention provides a method including receiving (i) multiple electrophysiological (EP) signals acquired by multiple electrodes of a multi-electrode catheter that are in contact with tissue in a region of a cardiac chamber, and (ii) respective tissue locations at which the electrodes acquired the EP signals. The region is divided into two sections. Using the EP signals acquired by the electrodes, local activation times (LAT) are calculated for the respective tissue locations, and found are: a first section of the two sections having a smaller average LAT value, and a second section of the two sections having a higher average value. Determined are a first representative location in the first section, and a second representative location in the second section. A propagation vector is calculated between the first and second representative locations, that is indicative of propagation of an EP wave that has generated the EP signals. The propagation vector is presented to a user.

In some embodiments, presenting the propagation vector includes overlaying an arrow on a map of the cardiac chamber. In other embodiments, overlaying the arrow includes using a graphical property of the arrow to indicate a speed of the EP wave between the first and second representative locations.

In some embodiments, the graphical property of the arrow includes one or more of a color, a length, a width, and a graphical pattern such as a gradient or dashes.

In an embodiment, the method further includes, in case of detecting a reentering EP wave, calculating an additional propagation vector for the reentering EP wave.

In another embodiment, the method further includes overlaying the additional arrow on a map of the cardiac chamber. In yet another embodiment, overlaying the additional arrow includes using a graphical property of the additional arrow to indicate at least one of a LAT difference and a cycle time of reentry of the reentering EP wave.

In some embodiments, determining the first representative location includes determining a tissue location having a smallest LAT value among the tissue locations in the first section, and wherein determining the second representative location includes determining a tissue location having a largest LAT value among the tissue locations in the second section.

In some embodiments, determining the first representative location includes calculating a first center-of-mass of the tissue locations in the first section, and wherein determining the second representative location includes calculating a second center-of-mass of the tissue locations in the second section.

In an embodiment, calculating the first center-of-mass includes calculating a first weighted average of the tissue locations in the first section using two or more of the LAT values of the first section as weights, and wherein calculating the second center-of-mass includes calculating a second weighted average of the tissue locations in the second section using two or more of the LAT values of the second section as weights.

There is additionally provided, in accordance with another embodiment of the present invention, a system including an interface and a processor. The interface is configured to receive (i) multiple electrophysiological (EP) signals acquired by multiple electrodes of a multi-electrode catheter that are in contact with tissue in a region of a cardiac chamber, and (ii) respective tissue locations at which the electrodes acquired the EP signals. The processor is configured to (a) divide the region into two sections, (b) using the EP signals acquired by the electrodes, calculate local activation time (LAT) values for the respective tissue locations, and find a first section of the two sections having a smaller average LAT value, and a second section of the two sections having a higher average value, (c) determine a first representative location in the first section, and a second representative location in the second section, (d) calculate between the first and second representative locations a propagation vector indicative of propagation of an EP wave that has generated the EP signals, and (e) present the propagation vector to a user.

The present invention will be more fully understood from the following detailed description of the embodiments thereof, taken together with the drawings in which:

DETAILED DESCRIPTION OF EMBODIMENTS

Overview

Figure 1:
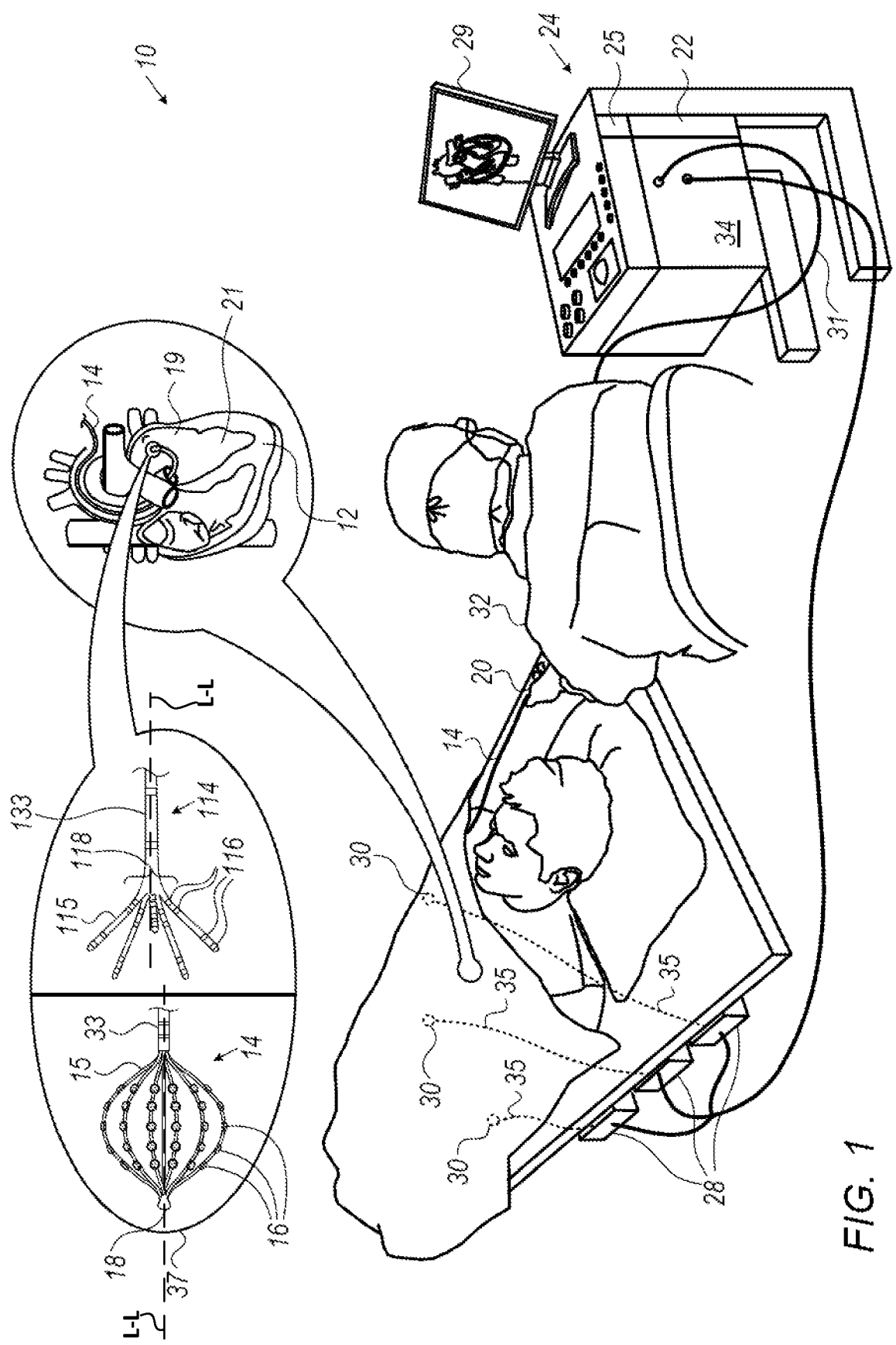
FIG. 1 is a schematic, pictorial illustration of an electrophysiological (EP) mapping system comprising different possible multi-electrode catheters, in accordance with embodiments of the present invention.

Intracardiac electrophysiological (EP) mapping is a catheter-based method that is sometimes applied to characterize cardiac EP wave propagation abnormalities, such those that cause an arrhythmia. In a typical catheter-based procedure, a distal end of a catheter, which comprises multiple sensing-electrodes, is inserted into the heart to sense a set of data points comprising measured locations over a wall tissue of a cardiac chamber and a respective set of EP signals, from which the EP mapping system can produce a map, such as an EP map, of the cardiac chamber.

For diagnostics in particular, the propagation direction of the EP wave at a region of the wall tissue may also be needed. The propagation direction of the cardiac wave can be found by creating a particular EP timing diagram map, called local activation time (LAT) map, of regions of the cardiac chamber.

However, determining a propagation vector of an EP wave in the cardiac chamber is a time-consuming process for any given region. Typically, LATs for a number of locations around the region need to be calculated, and then the vector derived from the LATs and the positions of the locations. Embodiments of the present invention that are described hereinafter provide efficient methods to acquire EP data and automatically calculate such a propagation vector in real time for a region in a cardiac chamber.

Among other features, the disclosed methods may use, in a particular way, various types of multi-electrode catheters, such as a basket catheter or a multi-arm catheter (e.g., PentaRay™ or OctaRay™, made by Biosense-Webster). The multi-electrode catheter is brought into contact with tissue (e.g., pressed against tissue) at a region of the cardiac chamber so that its "pole" (e.g., a distal tip where the spines of the basket connect, or from where the multiple arms originate) is on the chosen cardiac tissue region, and electrodes on the spines/arms are in contact with wall tissue at a tissue region of the cardiac chamber to acquire EP signals.

In an embodiment, to calculate a propagation vector, a processor first divides (e.g., arbitrarily divides) the cardiac tissue region where the electrode locations are into two sections, using a virtual plane containing the axis of the catheter. Then, using EP signals acquired from each electrode, the processor calculates the LAT values at the electrode locations (i.e., respective tissue locations) in each section to find a first section of the two sections having the smaller average LAT values, and a second section of the two sections having higher average value.

Then, the processor determines a first representative location in the first section, and a second representative location in the second section. The processor calculates between the first and second representative locations a propagation vector indicative of propagation of an EP wave that has generated the EP signals, and presents the propagation vector to a user.

In one embodiment, for the section with the lower average LAT value, the processor finds the location with the minimum LAT value therein. For the section with the higher average LAT value, the processor finds the location with the maximum LAT value therein. From the known displacements (distance and direction) between the two locations, and the respective known time difference in LAT values, the processor calculates a propagation (e.g., velocity) vector (speed and direction) of the EP wave. The processor may then draw an arrow, corresponding to the vector, on a map of the cardiac chamber. The length of the arrow, its color or a graphical pattern (e.g., gradient or hatched patterns) may be set to correspond to the speed.

In another embodiment, rather than calculate the velocity vector from the minimum of the LAT values at the section with the lower average LAT value to the maximum of the LAT values at the section with the higher average LAT value, the processor calculates a vector between a center-of-mass wall tissue location of the lower average LAT value and a center-of-mass wall tissue location of the higher average LAT value. To this end, the processor performs a center-of-mass calculation in the first section of a first wall tissue location of the lower average LAT value and a center-of-mass calculation in the second section of a second wall tissue location of the higher average LAT value. Then the processor calculates a center-of-mass propagation vector between the first and second center-of-mass locations of an EP wave that presumably generated the EP signals, and presents the center-of-mass propagation vector to a user. The center-of-mass calculations typically include calculating a weighted average of each center-of-mass location using two or more LAT values of each section as weights.

In some clinical cases, such as in a reentry type of arrhythmia, while the catheter is in an approximately fixed position, the velocity vector oscillates in direction (backwards and forwards). This occurs typically if the catheter is at a junction, where the wave actually alternates in direction, for example, due to the wave encountering aberrant unidirectional propagation-blocking tissue. In this case the processor calculates an additional vector, and the two vectors may be displayed on the screen as two arrows distinguished by a different brightness/thickness/length/color according to their relative magnitude.

Typically, the processor is programmed in software containing a particular algorithm that enables the processor to conduct each of the processor-related steps and functions outlined above.

The disclosed systems and methods for efficient derivation and clear presentation of propagation direction(s) of an EP wave may improve catheter-based arrhythmia diagnostics and treatment procedures.

System Description

FIG. 1 is a schematic, pictorial illustration of an electrophysiological (EP) mapping system 10 comprising different possible multi-electrode catheters, in accordance with embodiments of the present invention. System 10 may be configured to analyze substantially any physiological parameter or combinations of such parameters. In the description herein, by way of example, the analyzed signals are assumed to be intra-cardiac electrogram potential-time relationships. In order to fully characterize such relationships, the signals at various locations need to be referenced in time to each other, such as is done during LAT map generation. The time referencing is accomplished by measuring relative to a reference time (e.g., an instance in time), such as the beginning of each QRS complex of an ECG reference signal (i.e., the beginning of every heartbeat). The method for generating an LAT map is described in U.S. Pat. No. 9,050,011, cited above.

As noted above, system 10 comprises a multi-electrode catheter, which can be, among numerous possible options, a basket catheter 14 or a multi-arm catheter 114 (e.g., a PentaRay™ catheter), both of which are shown in inset 37. The description hereinafter collectively calls the above catheter options, "catheter 14/114," which means the embodiments described hereinafter hold for either of these multi-electrode catheter types. Each catheter tip 14, 114 extends along longitudinal axis L-L.

Multi-electrode catheter 14/114 is inserted by a physician 32 through the patient's vascular system into a chamber or vascular structure of a heart 12. Physician 32 brings the catheter's distal tip 18/118 into contact with (e.g., presses the tip distally against) wall tissue 19 of a cardiac chamber 21, at an EP mapping target tissue site. The catheter typically comprises a handle 20 which has suitable controls to enable physician 32 to steer, position and orient the distal end of the catheter as desired for EP mapping.

The multi-electrode catheter 14/114 is coupled to a console 24, which enables physician 32 to observe and regulate the functions of the catheter. To aid physician 32, the distal portion of the catheter may contain various sensors, such as contact force sensors (not shown) and a magnetic sensor 33/133 that provides position, direction, and orientation signals to a processor 22, located in a console 24. Processor 22 may fulfill several processing functions as described below. In particular, electrical signals can be conveyed to and from heart 12 from electrodes 16/116 located at or near the distal tip 18 of catheter 14/114 via cable 34 to console 24. Pacing signals and other control signals may be conveyed from console 24 through cable 34 and electrodes 16/116 to heart 12.

Console 24 includes a monitor 29 driven by processor 22. Signal processing circuits in an electrical interface 34 typically receive, amplify, filter, and digitize signals from catheter 14/114, including signals generated by the above-noted sensors and the plurality of sensing electrodes 16. The digitized signals are received and used by console 24 and the positioning system to compute the position and orientation of catheter 14/114 and to analyze the EP signals from electrodes 16/116 as described in further detail below.

During the disclosed procedure, the respective locations of electrodes 16/116 are tracked. The tracking may be performed, for example, using the CARTO® 3 system, produced by Biosense-Webster. Such a system measures impedances between electrodes 16/116 and a plurality of external electrodes 30 that are coupled to the body of the patient. For example, three external electrodes 30 may be coupled to the patient's chest, and another three external electrodes may be coupled to the patient's back. (For ease of illustration, only chest electrodes are shown in FIG. 1). Wire connections 35 link the console 24 with body surface electrodes 30 and other components of a positioning subsystem to measure location and orientation coordinates of catheter 14/114. The method of tracking electrode 16 positions based on electrical signals, named Active Current Location (ACL), is implemented in various medical applications, as, for example, the aforementioned CARTO®3 system. Details of an ACL subsystem and process are provided in U.S. Pat. No. 8,456,182, which is assigned to the assignee of the present patent application and whose disclosure is incorporated herein by reference with a copy provided in the Appendix.

In some embodiments, system 10 comprises, in addition to, or instead of, the ACL tracking subsystem, a magnetic position tracking subsystem that determines the position and orientation of magnetic sensor 33, at a distal end of catheter 14/114, by generating magnetic fields in a predefined working volume, and sensing these fields at the catheter using field generating coils 28. As electrodes 16/116 have known locations on arms 15/115, and known relationships to one another, once catheter 14/114 is tracked magnetically in the heart, the location of each of electrodes 16/116 in the heart becomes known. A suitable magnetic position tracking subsystem is described in U.S. Pat. Nos. 7,756,576 and 7,536,218, which are assigned to the assignee of the present patent application and whose disclosure is incorporated herein by reference with a copy provided in the Appendix.

Based on the EP signals from electrodes 16/116 having tracked locations, electrical activation maps may be prepared, according to the methods disclosed in U.S. Pat. Nos. 6,226,542, and 6,301,496, and 6,892,091, which are assigned to the assignee of the present patent application and whose disclosure is incorporated herein by reference with a copy provided in the Appendix.

Processor 22 uses software stored in a memory 25 to operate system 10. The software may be downloaded to processor 22 in electronic form, over a network, for example, or it may, alternatively or additionally, be provided and/or stored on non-transitory tangible media, such as magnetic, optical, or electronic memory. In particular, processor 22 runs a dedicated algorithm as disclosed herein, including in FIG. 4, that enables processor 22 to perform the disclosed steps, as further described below.

The example illustration shown in FIG. 1 is chosen purely for the sake of conceptual clarity. Other types of EP sensing geometries, such as of a balloon catheter comprising electrode segments, described in U.S. patent application Ser. No. 16/708,285, titled, "Catheter with Plurality of Sensing Electrodes Used as Ablation Electrodes," filed Dec. 9, 2019, whose disclosure is incorporated herein by reference (with a copy in the Appendix), may also be employed.

System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation of tissue of heart 12.

Figure 2B:
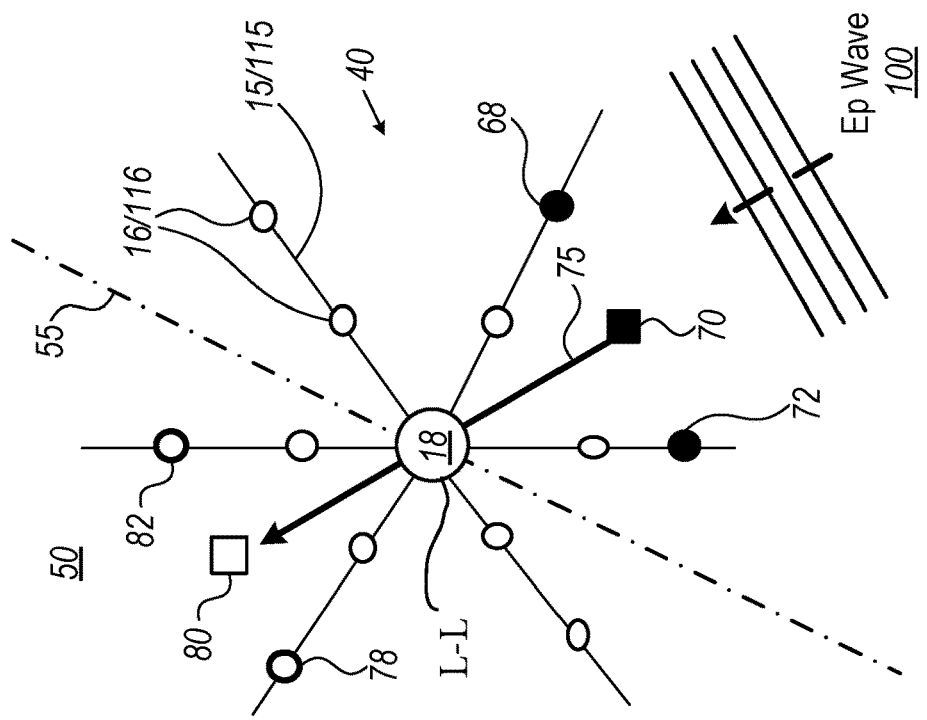
FIGS. 2A and 2B are schematic distal views of electrodes of one of the catheters of FIG. 1 in contact with tissue and measuring electrophysiological (EP) signals, in accordance with embodiments of the present invention.
Figure 2A:
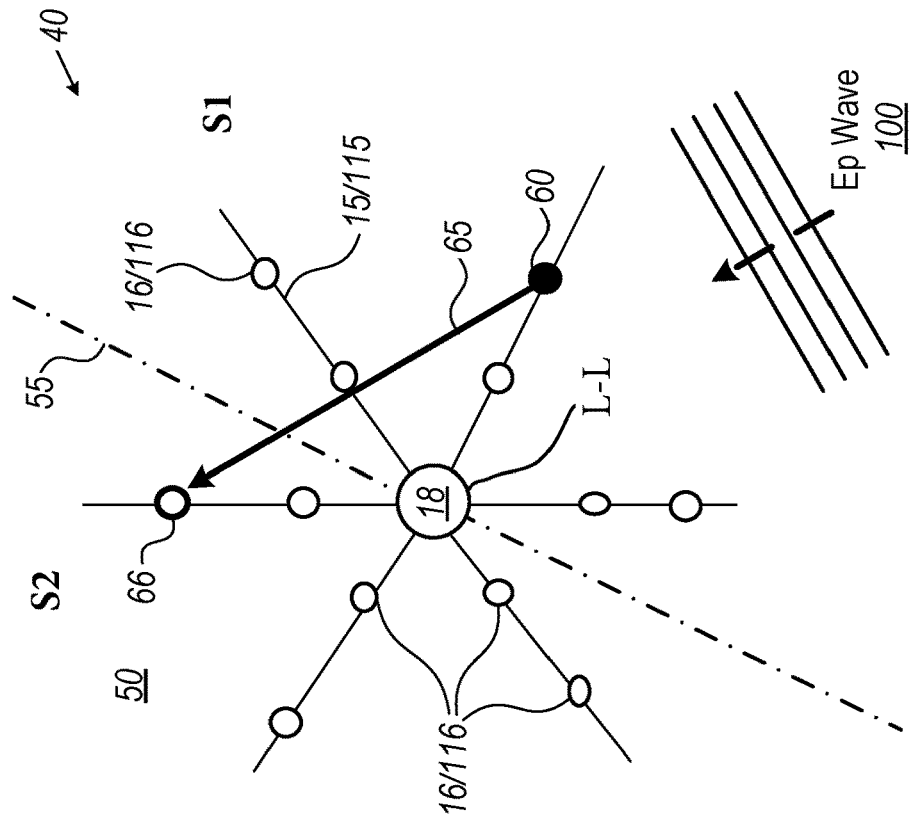

Analyzing Multi-Electrode Catheter Signals to Determine Ep Wave Propagation Vector FIGS. 2A and 2B are schematic distal views of electrodes 16/116 of one of the catheters of FIG. 1 in contact with tissue and measuring electrophysiological (EP) signals, in accordance with embodiments of the present invention. The figures further show tissue 50 and a distal portion 40 of the spines or arms 15/115 of catheter 14/114 that are pressed against tissue 50, as viewed at a distal direction from a location proximally to the spines or arms on the axis L-L of the catheter. The spines or arms 15/115 are coupled together at distal tip 18/118 of the catheter.

In some embodiments, processor 22 divides the spines/arms into two sections, using a virtual plane 55 containing the axis L-L of the catheter. Processor 22 may select the sections, i.e., select plane 55, arbitrarily or in accordance with a certain selection criterion. For example, the virtual plane 55 is configured to intersect with the central longitudinal axis L-L of the catheter and may not intersect with any of the spine or arm of catheter 14 or 114. Then, using EP signals acquired from each electrode 16/116, the processor calculates the LAT values at the electrode locations in each section. Processor 22 then finds which of the two sections (S1 or S2) is characterized by lower average LAT values (e.g., has the lower average LAT value out of the two sections), and which is characterized by higher average LAT values (e.g., has the higher average value out of the two sections).

In the embodiment shown in FIG. 2A, virtual plane 55 separates the spines or arms into two sections, a first section S1 with the lower average LAT value and another or second section S2 with a higher average LAT value. The first section S1 is determined by the processor to find the minimum LAT value, and its location is determined to be at point 60 (which may be the location of a sensing electrode on the spine or arm of a catheter 14 or 114). For the other or second section S2 with the higher average LAT value, the processor finds the maximum LAT value, and its location 66 (which may be the location of a sensing electrode on the spine or arm of a catheter 14 or 114). Locations 60 and 66 are referred to herein as "representative locations" because each of them represents its entire respective section by a single data point.

From the known displacements (distance and direction) between the two representative locations, and the known times (the difference in LAT values), the processor calculates a velocity vector (speed and direction) of an EP wave 100 that generated the signals as it propagates in tissue under the catheter. The processor may then draw an arrow 65, corresponding to the vector, on a map of the cardiac chamber and provide this in display screen 29. The length of arrow 65, and/or its color, may be set to correspond to the speed.

In the embodiment shown in FIG. 2B, rather than calculating the velocity vector from the minimum of the LAT values at the section with the lower average LAT value to the maximum of the LAT values at the section with the higher average LAT value, the vector is calculated between the centers-of-mass locations of the lower average and higher average LAT values, using the following equation to find the center of mass locations:

$$\bar{r} = \frac{\sum_i LAT_i r_i}{\sum_i LAT_i} \quad \text{Eq. 1}$$

In FIG. 2B, by way of example, i=1, 2 for each center of mass location. That is, center-of-mass wall tissue location 70 is calculated from Eq. 1 using LAT values and respective locations 68 and 72, and center-of-mass wall tissue location 80 is calculated using LAT values and respective locations 78 and 82. The processor may then draw an arrow 75 corresponding to the vector between locations 70 and 80. Thus, in the example of FIG. 2B, the centers-of-mass of the two sections (locations 70 and 80) serve as the representative locations. In alternative embodiments, processor 22 may choose the representative locations in the two sections in any other suitable way.

The illustrations in FIGS. 2A and 2B are conceptual and brought by way of example. Actual catheter structure may vary. For example, the number of spines or arms may be larger than shown.

Figure 3:
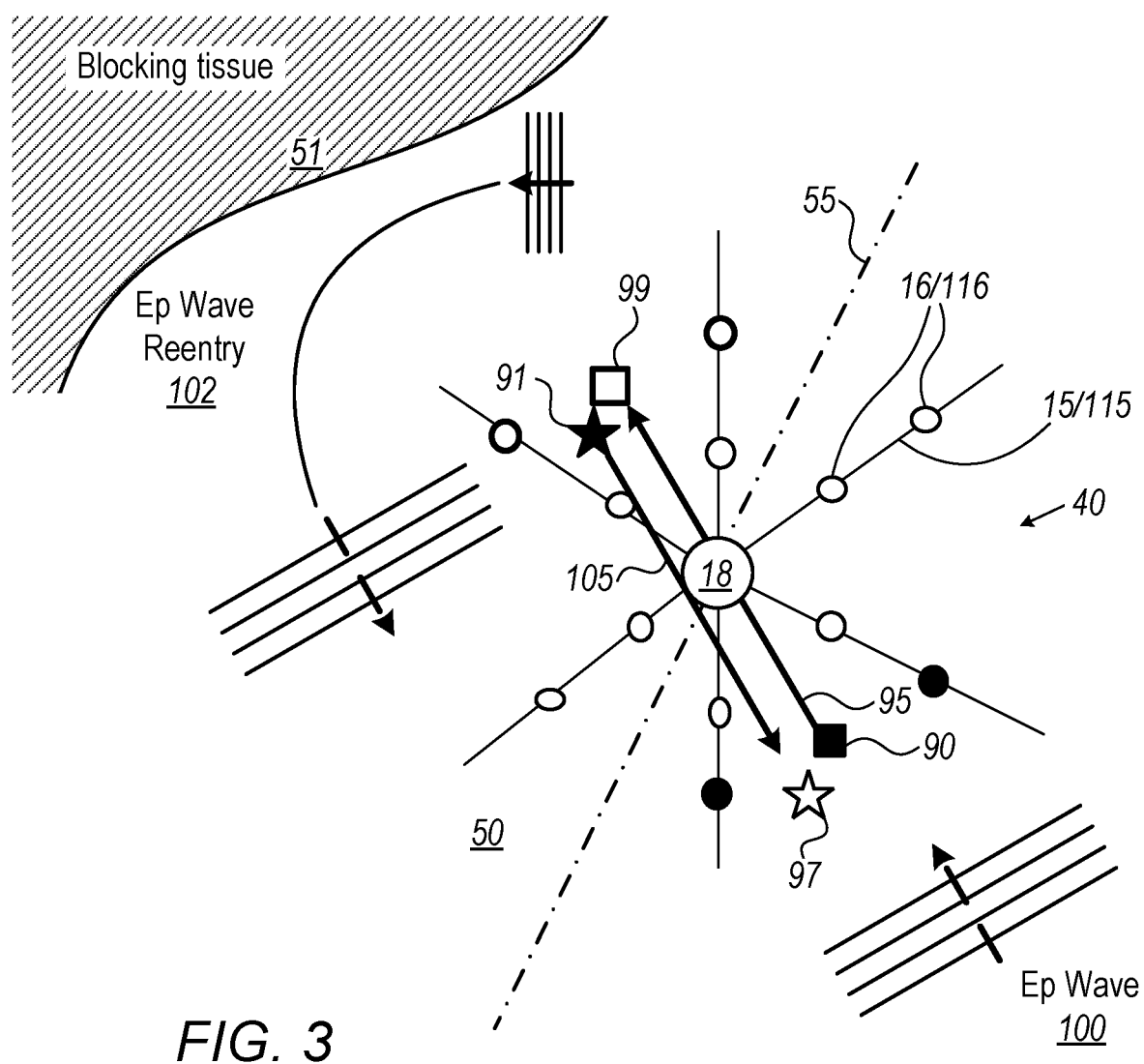
FIG. 3 is a schematic distal view of electrodes of one of the catheters of FIG. 1 in contact with tissue and measuring electrophysiological (EP) signals, in accordance with another embodiment of the present invention.

FIG. 3 is a schematic distal view of electrodes 16/116 of one of the catheters of FIG. 1 in contact with tissue and measuring electrophysiological (EP) signals, in accordance with another embodiment of the present invention. The catheter 14/114 layout is the same as in FIGS. 2A and 2B, but with the catheter placed at a different tissue location where EP wave reentry occurs.

As noted above, in case of a reentry type of arrhythmia, the velocity vector at the region may oscillate in direction (backwards and forwards). This occurs typically if the catheter is at a junction where EP wave 100 is actually alternating in direction, for example, due to the wave encountering an aberrant unidirectional propagation blocking tissue 52. In this case, the two EP wave vectors (one of incident EP wave 100 and the other of reentry EP wave 102) may be displayed on the screen as two respective arrows, 95 and 97, each with a different brightness/thickness/length/color according to their relative magnitudes. In FIG. 3 the vectors are calculated using the center-of-mass calculation method of FIG. 2B. One respective vector points from center-of-mass location 90 to center-of-mass location 99, and the other from center-of-mass location 91 to center-of-mass location 97.

Figure 4:
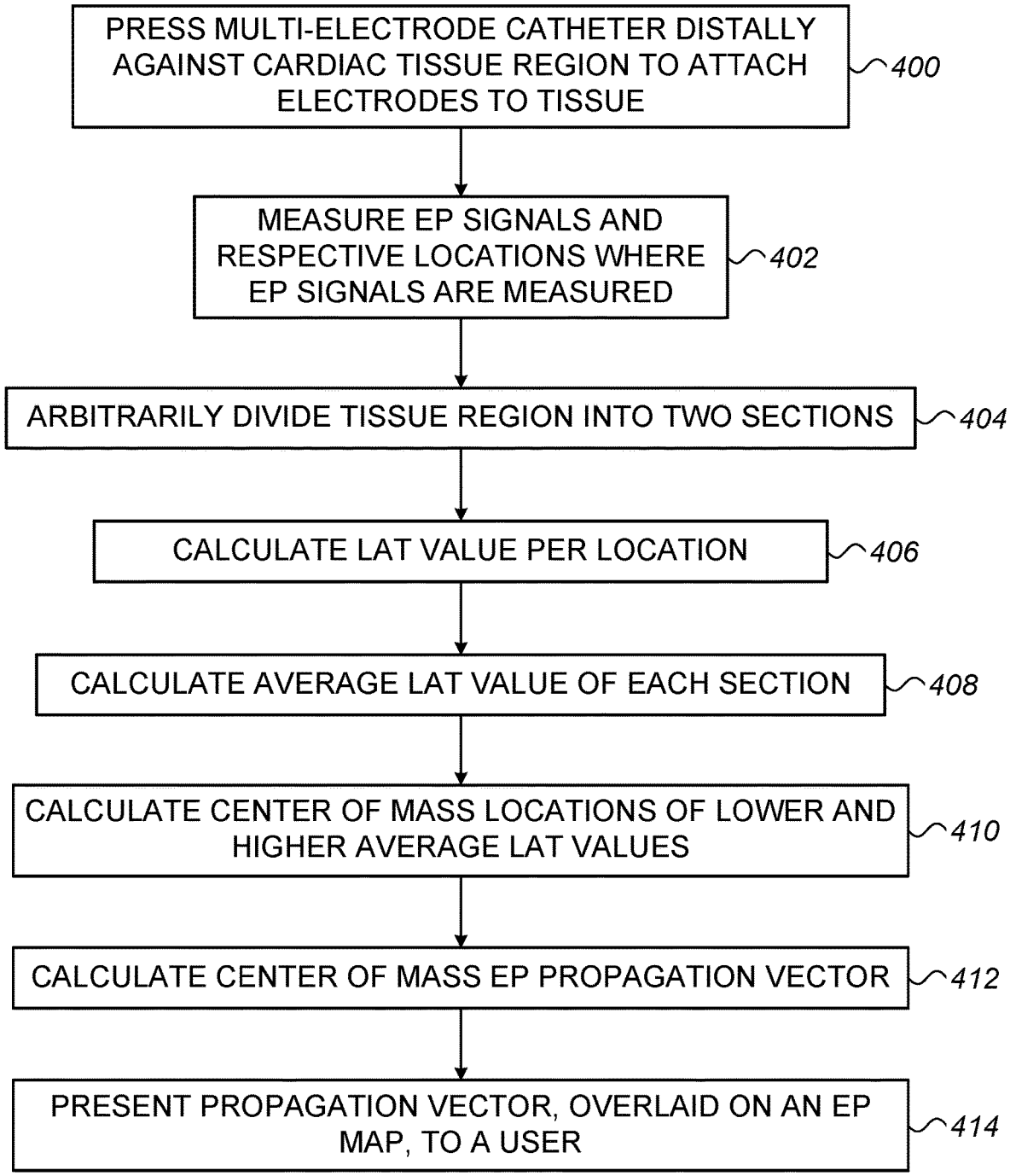
FIG. 4 is a flow chart that schematically illustrates a method and algorithm for estimating and presenting a propagation vector of an electrophysiological (EP) wave, in accordance with an embodiment of the present invention.

FIG. 4 is a flow chart that schematically illustrates a method and algorithm for estimating and presenting a propagation vector of an electrophysiological (EP) wave 100, in accordance with an embodiment of the present invention. The algorithm, according to the presented embodiment, carries out a process that begins with physician 30 pressing catheter 14/114 against cardiac tissue region to bring part of electrodes 16/116 to contact with tissue, at a catheter placement step 400.

Then, system 10 measures electrode locations over wall tissue 19 of cardiac chamber 21 and a respective set of EP signals at the locations, generated by an EP wave 100, at a measurement step 402.

Next, processor 22 arbitrarily divides the region into two sections, at a region division step 404.

Next, processor 22 calculates an LAT value at each electrode location, at an LAT calculation step 406.

Next, at average LAT calculation step 408, processor 22 calculates the average LAT value per each section. Typically, one section has a lower average LAT value than the other.

Next, at average LAT location calculation step 410, processor 22 calculates center-of-mass locations of the lower and higher average LAT values, using the method described in FIG. 2B.

Using the center-of-mass locations, processor 22 calculates the center-of-mass EP wave propagation vector of EP wave 100, at a vector calculation step 414.

Finally, at a propagation-vector presentation step 410, processor 22 overlays (e.g., draws) an arrow, corresponding to the vector, on a map of the cardiac chamber as shown on display 29 in FIG. 1. The length of the arrow 65 or 75, and/or its color, may be set to correspond to the speed.

The example flow chart shown in FIG. 4 is chosen purely for the sake of conceptual clarity. The present embodiment also comprises additional steps of the algorithm, such as operating other sensors mounted on the catheter, such as contact force sensors, which have been omitted from the disclosure herein purposely on order to provide a more simplified flow chart.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   receiving: (i) multiple electrophysiological (EP) signals acquired by multiple electrodes of a multi-electrode catheter that are configured to be in contact with tissue in a region of a cardiac chamber, and (ii) respective tissue locations at which the electrodes acquired the EP signals;
   calculating an average local activation time (LAT) for a plurality of selected tissue sections from the EP signals acquired by the multi-electrode catheter;
   determining a first section of the plurality of selected tissue sections having a smallest average LAT value, and a second section of the plurality of selected tissue sections having a highest average LAT value;
   determining a first representative location in the first section, and a second representative location in the second section;
   calculating between the first and second representative locations a propagation vector indicative of propagation of an EP wave that has generated the EP signals;
   outputting the propagation vector to a display in a graphical form;
   determining that a re-entering EP wave was detected; and
   calculating an additional propagation vector for the re-entering EP wave.

2. The method according to claim 1, wherein determining the first representative location comprises determining a tissue location having a smallest LAT value among the tissue locations in the first section, and wherein determining the second representative location comprises determining a tissue location having a largest LAT value among the tissue locations in the second section.

3. The method according to claim 2, wherein calculating a propagation vector indicative of propagation of an EP wave comprises determining a speed and a direction of the EP wave.

4. The method according to claim 1, wherein presenting the propagation vector comprises overlaying an arrow on a map of the cardiac chamber.

5. The method according to claim 4, wherein overlaying the arrow comprises using a graphical property of the arrow to indicate a speed of the EP wave between the first and second representative locations.

6. The method according to claim 5, wherein the graphical property of the arrow comprises one or more of a color, a length, a width, or a graphical pattern.

7. The method according to claim 1, wherein determining the first representative location comprises calculating a first center-of-mass of the tissue locations in the first section, and wherein determining the second representative location comprises calculating a second center-of-mass of the tissue locations in the second section.

8. The method according to claim 7, wherein calculating the first center-of-mass comprises calculating a first weighted average of the tissue locations in the first section using two or more of the LAT values of the first section as weights, and wherein calculating the second center-of-mass comprises calculating a second weighted average of the tissue locations in the second section using two or more of the LAT values of the second section as weights.

9. The method according to claim 1, further comprising:
   detecting a re-entering EP wave and calculating an additional propagation vector for the re-entering EP wave.

10. The method according to claim 9, further comprising:
    overlaying a first arrow indicative of the propagation vector of the EP wave on a map of the cardiac chamber; and
    overlaying a second arrow indicative of the additional propagation vector of the re-entering EP wave on the map of the cardiac chamber.

11. The method according to claim 10, wherein overlaying the second arrow comprises using a graphical property of the second arrow to indicate at least one of a LAT difference and a cycle time of reentry of the re-entering EP wave.

12. A system, comprising:
    one or more processors; and
    a memory in communication with the one or more processors and storing instructions that, when executed by the one or more processors, are configured to cause the system to:
       receive: (i) multiple electrophysiological (EP) signals acquired by multiple electrodes of a multi-electrode catheter that are configured to be in contact with tissue in a region of a cardiac chamber, and (ii) respective tissue locations at which the electrodes acquired the EP signals;
       calculate an average local activation time (LAT) for a plurality of selected tissue sections from the EP signals acquired by the multi-electrode catheter;
       determine a first section of the plurality of selected tissue sections having a smaller average LAT value, and a second section of the plurality of selected tissue sections having a higher average LAT value;
       determine a first representative location in the first section, and a second representative location in the second section;
       calculate between the first and second representative locations a propagation vector indicative of propagation of an EP wave that has generated the EP signals;
       determine if a re-entering EP wave is detected; and calculate an additional propagation vector for the re-entering EP wave.

13. The system according to claim 12, wherein the instructions are further configured to cause the system to output the propagation vector to a display to present the propagation vector to a user.

14. The system according to claim 13, wherein the instructions are further configured to cause the system to:
render to the display a map of the cardiac chamber; and
present the propagation vector by overlaying an arrow on the map of the cardiac chamber.

15. The system according to claim 14, wherein calculating a propagation vector indicative of propagation of an EP wave comprises determining a speed and a direction of the EP wave.

16. The system according to claim 15, wherein the instructions are further configured to cause the system to use a graphical property of the arrow to indicate a speed of the EP wave between the first and second representative locations.

17. The system according to claim 14, wherein the instructions are further configured to cause the system to
overlay an additional arrow indicative of the propagation vector on a map of the cardiac chamber; and
use a graphical property of the additional arrow to indicate at least one of a LAT difference and a cycle time of reentry of the re-entering EP wave, wherein the graphical property of the arrow comprises one or more of a color, a length, a width, or a graphical pattern.

18. The system according to claim 12, wherein the instructions are further configured to cause the system to determine the first representative location by determining a tissue location having a smallest LAT value among the tissue locations in the first section, and to determine the second representative location by determining a tissue location having a largest LAT value among the tissue locations in the second section.

19. The system according to claim 12, wherein the instructions are further configured to cause the system determine the first representative location by calculating a first center-of-mass of the tissue locations in the first section, and to determine the second representative location by calculating a second center-of-mass of the tissue locations in the second section.

20. The system according to claim 19, wherein the instructions are further configured to cause the system to calculate the first center-of-mass by calculating a first weighted average of the tissue locations in the first section using two or more of the LAT values of the first section as weights, and calculate the second center-of-mass by calculating a second weighted average of the tissue locations in the second section using two or more of the LAT values of the second section as weights.

* * * * *